United States Patent [19]

Innes et al.

[11] 4,057,570

[45] Nov. 8, 1977

[54] PROCESS FOR PREPARING ACRYLONITRILE

[75] Inventors: Robert A. Innes, Pittsburgh; Anthony J. Perrotta, Monroeville, both of Pa.

[73] Assignee: Gulf Research & Development Company, Pittsburgh, Pa.

[21] Appl. No.: 715,281

[22] Filed: Aug. 18, 1976

Related U.S. Application Data

[63] Continuation-in-part of Ser. No. 645,419, Dec. 30, 1975.

[51] Int. Cl.$^2$ .......................................... C07C 120/14
[52] U.S. Cl. .................................................. 260/465.3
[58] Field of Search ...................................... 260/465.3

[56] References Cited

U.S. PATENT DOCUMENTS

| | | | |
|---|---|---|---|
| 3,198,750 | 8/1965 | Callahan et al. | 260/465.3 X |
| 3,308,151 | 3/1967 | Callahan et al. | 260/465.3 |
| 3,328,315 | 6/1967 | Callahan et al. | 260/465.3 X |
| 3,431,292 | 3/1969 | Callahan et al. | 260/465.3 |
| 3,849,337 | 11/1974 | Manara et al. | 260/465.3 X |

*Primary Examiner*—Joseph Paul Brust

[57] ABSTRACT

A process for preparing acrylonitrile using novel compounds containing critical amounts of uranium, antimony and an element from Group IV B of the Periodic Table.

13 Claims, No Drawings

PROCESS FOR PREPARING ACRYLONITRILE

This application is a continuation-in part application of our application Ser. No. 645,419, entitled Oxidation Catalysts and Process for Preparing Same, filed Dec. 30, 1975.

BACKGROUND OF THE INVENTION

1. Field of the Invention

This invention is directed to a process for preparing acrylonitrile using novel compounds containing critical amounts of uranium, antimony and an element from Group IV B of the Periodic Table.

2. Description of the Prior Art

Oxidation catalysts consisting essentially of oxides of antimony and uranium are old and well known. Such catalysts and their uses are described in U.S. pat. Nos. 3,198,750 and 3,308,151 to Callahan and Gertisser. Antimony-uranium oxide catalysts are used primarily for converting propylene, in the presence of ammonia and a gas containing molecular oxygen, to acrylonitrile. Other uses include the ammoxidation of isobutylene to methacrylonitrile and the oxidative conversions of propylene to acrolein, isobutylene to methacrolein, butene-1 or butene-2 to 1,3-butadiene, and isoamylenes to isoprene. It has been shown by Grasselli and Callahan in the *Journal of Catalysis*, 14, 93–103 (1969) that the most effective catalysts are obtained when the antimony to uranium atomic ratio is greater than three. Their best catalyst had an antimony to uranium atomic ratio of 4.6. The sole uranium containing phase detected in this catalyst was $USb_3O_{10}$ according to Grasselli and Suresh, *Journal of Catalysis*, 25, 273–291 (1972). The excess antimony oxide insured that undesirable uranium-containing phases, such as $USbO_5$ and $U_3O_8$ were not formed. U.S. Pat. No. 3,816,596 to Wise describes a method of making a catalyst consisting essentially of $USb_3O_{10}$. Antimony-uranium oxide catalysts may be made attrition resistant by adding silica as described in U.S. Pat. No. 3,341,471 to Callahan et al.

Attempts have been made to improve the antimony-uranium oxide catalyst by combining the optimum antimony-uranium oxide composition with the oxides of most of the metallic elements of the Periodic Table. See, for example, U.S. Pat. Nos. 3,328,315 and 3,431,292 to Callahan et al and British Pat. No. 1,007,929 to Distiller's Company Limited. Based on starting materials, every catalyst tested in these patents had an antimony to uranium atomic ratio of 4.0 or 4.6, i.e. close to the optimum composition of Grasselli and Callahan.

SUMMARY OF THE INVENTION

We have found that if we heat for a sufficient length of time at a temperature of at least about 850° C. an intimate mixture containing (1) the oxides of uranium, antimony and an element from Group IV B of the Periodic Table (titanium, zirconium or hafnium) or (2) compounds of said elements that will decompose or will otherwise be converted to said oxides at said temperature, wherein the atomic ratios of said elements are within selected critical ranges, preferably in molecular oxygen, such as air, we obtain a compound, believed to be crystalline, in which said elements and oxygen are chemically combined within selected critical atomic ratios, which compound is more highly active as an oxidation catalyst than the prior art catalysts referred to above and which exhibits excellent selectivity in the production of acrylonitile from propylene.

Examples of oxides that can be heated as part of the mixture described above include $UO_2$, $U_3O_8$, $UO_3$, $Sb_2O_3$, $Sb_2O_4$, $Sb_2O_5$, $Ti_2O_3$, $TiO_2$, $ZrO_2$, $HfO_2$, $UTiO_5$, $USbO_5$, $USb_3O_{10}$, etc. Examples of compounds that will be converted to these oxides upon heating include $UO_2(NO_3)_2 \cdot 6H_2O$, $UO_2C_2O_4 \cdot 3H_2O$, $UO_2(C_2H_3O_2)_2 \cdot 2H_2O$, $Sb_2(C_4H_4O_6)_3 \cdot 6H_2O$, $Sb(C_2H_3O_2)_3$, $(NH_4)_2TiO(C_2O_4)_2 \cdot H_2O$, $Ti_2(C_2O_4)_3 \cdot 10H_2O$, $Zr(C_2H_3O_2)_4$, $ZrO(C_2H_3O_2)_2$, and any hydrated oxide or hydroxide of antimony, uranium, titanium, zirconium or hafnium.

Intimate mixing of the above materials greatly facilitates the formation of the desired crystalline phase. In a preferred embodiment of our invention, intimate mixing is achieved, for example, by co-precipitation of the hydroxides or hydrated oxides from acidic solution by adding a suitable base, such as ammonium hydroxide. The precipitate so obtained is washed with water, dried at a temperature of 100°–200° C. for from about two to about 24 hours and then calcined. The acidic solution is conveniently prepared using various soluble salts as starting materials. These include $UO_2(NO_3)_2 \cdot 6H_2O$, $UO_2(C_2H_3O_2)_2 \cdot 2H_2O$, $UCl_3$, $UCl_4$, $UF_6$, $UBr_4$, $SbCl_3$, $Sb(C_2H_3O_2)_3$, $SbF_3$, $SbCl_5$, $Ti_2(C_2O_4)_3 \cdot 10H_2O$, $ZrOCl_2 \cdot 8H_2O$, $ZrO(C_2H_3O_2)_2$, and $ZrOBr_2 \cdot XH_2O$. Alternatively, one can prepare acidic solutions from the metals themselves or their oxides. For example, Sb metal can be reacted with concentrated nitric acid to obtain the hydrous oxide, which can then be dissolved in concentrated hydrochloric acid.

The amounts of the reactant components used in the preparation of the catalyst herein are critical. Thus the metals in the reactant components must be present in amounts such that the atomic ratio of antimony to uranium is at least about 1.35:1, preferably at least about 1.50:1, but no higher than about 2.75:1, preferably no higher than about 2.5:1, the atomic ratio of the Group IV B element to uranium is at least about 0.25:1, preferably at least about 0.5:1, but no higher than about 1.65:1, preferably no higher than about 1.5:1. In addition the atomic ratios of the sum of the antimony and the Group IV B element to uranium must be within a range of about 3.5:1 to about 2.5:1, preferably about 3.3:1 to about 2.8:1, with the most preferred range being about 3:1. We have found that such reactant amounts are critical if we are to obtain the new chemical compounds herein having the critical amounts of uranium, antimony, Group IV B element and oxygen, namely a crystalline compound falling within the following formula:

$USb_{3-x}A_xO_{9-10}$, wherein A is a Group IV B element, namely, titanium, zirconium or hafnium, $x$ is the number about 0.25 or higher, preferably about 0.5 or higher, but no higher than about 1.50, preferably no higher than about 1.25. If amounts outside the defined reactants amounts are used in the attempted preparation of the new compound, the new compound defined above is either not obtained or if it is obtained appreciable amounts of other undesirable compounds containing one or more of the elements present in the reaction mixture, such as $TiO_2$, $UTiO_5$, $USbO_5$, $USb_3O_{10}$, $U_3O_8$, $Sb_2O_4$, $Sb_2O_5$, $ZrO_2$, $HfO_2$, etc., are also obtained. Compounds that can form in addition to the novel compounds when the critical amounts of reactant components are not used cannot easily be separated from the novel compounds. The resultant mixture will have a relatively low activity or poorer selectivity or both.

Once the critical amounts of reactant components are selected, the reaction mixture containing the same must be heated (calcined) to a critical temperature of at least about 850° C., preferably at least about 875° C., preferably in an atmosphere containing molecular oxygen, in order to obtain the defined novel compound. Although the temperature can be as high as about 1050° C., or even higher, in general a temperature of about 1000° C. need not be exceeded. Once having selected a critical temperature within the above range, the mixture is maintained at such temperature for a time sufficient to crystallize the new compounds herein. At the lower temperatures, longer calcination periods are required, while at the higher temperatures lower periods will suffice. Thus, the time required for calcination can be as low as about 15 minutes, generally at least about one hour, but a period of no more than about 24 hours, generally no more than about 18 hours, will suffice. The heating is carried out at atmospheric pressure, although elevated pressures can be used if desired.

The catalyst obtained herein can be employed as an oxidation catalyst using conventional procedures. Thus, in the conversion of propylene to acrylonitrile, in the presence of ammonia and a gas containing molecular oxygen, such as air or oxygen itself, a gaseous mixture containing such reactants is brought into contact with the novel catalyst compound defined herein at a pressure of about 0 to about 100 pounds per square inch gauge (about 0 to about 7.0 kilograms per square centimeter), preferably about 0 to about 50 pounds per square inch gauge (about 0 to about 3.5 kilograms per square centimeter), at an elevated temperature, that is, in a temperature range of about 375° to about 525° C., preferably about 450° to about 495° C., and at a contact time of at least about 0.01 second, preferably in the range of about 0.1 to about 15 seconds. The reaction mixture can optionally include a diluent, such as steam, to obtain increased selectivity to acrylonitrile. The molar ratio of oxygen to propylene is about 0.5:1 to about 5:1, preferably about 1:1 to about 2:1, while the molar ratio of ammonia to propylene is greater than about 0.9:1 but preferably no greater than about 1.5:1. By contact time we mean the bulk volume of the catalyst in cubic centimeters divided by the flow rate of the total reactants in vapor form at reaction conditions in cubic centimeters per second. The novel catalyst herein can be used in a fixed-bed or a fluidized-bed reactor.

DESCRIPTION OF PREFERRED EMBODIMENTS

The following will provide a further understanding of the invention claimed herein.

EXAMPLE I

To a flask equipped with a mechanical stirrer and containing 80.3 grams of $Sb_2O_3$ there was added 321 ml. of concentrated nitric acid and the mixture was refluxed for one-half hour. Meanwhile a solution of 60.2 grams of $UO_2(NO_3)_2 \cdot 6H_2O$ in 100 ml. of hot distilled water was prepared. The latter solution was then added to the flask and refluxing was continued for another three hours. The mixture was then brought to a pH of 8.0 by the addition thereto of concentrated ammonium hydroxide. The resulting precipitate was recovered by filtration, dried in an oven for 16 hours at a temperature of 120° C. and then calcined in air at a temperature of 900° C. for 16 hours. The product by X-ray diffraction was found not to be a single phase but contained the following crystalline compounds: $USb_3O_{10}$ and $Sb_2O_4$.

EXAMPLE II

To a solution containing 100 cc. of water and 6.84 grams of $SbCl_3$ there was first added 40 cc. of concentrated HCl and then a solution containing 100 cc. of water and 5.02 grams of $UO_2(NO_3)_2 \cdot 6H_2O$. The hydrous metal oxides were precipitated from solution by the addition thereto of 120 cc. of concentrated ammonium hydroxide. The precipitate obtained was filtered, washed with one liter of water and then placed in a drying oven for about 16 hours at a temperature of 120° C. The dried precipitate was then calcined in air at a temperature of 910° C. for 16 hours. In this example, as well as in those following, the preparation was carried out at atmospheric pressure and, unless otherwise stated, at atmospheric temperature. The product obtained, amounting to 7.05 grams, was shown by X-ray diffraction patterns to be the crystalline chemical compound $USb_3O_{10}$, with only small amounts (less than about 10 weight percent, based on the total compounds produced) of $Sb_2O_4$ and $USbO_5$.

EXAMPLE III

To a solution containing 100 cc. of water there was first added 5.48 grams of $SbCl_3$ and 5.02 grams of $UO_2(NO_3)_2 \cdot 6H_2O$, followed by 40 cc. of concentrated HCl and then a solution containing 1.62 grams of $Ti_2(C_2O_4)_3 \cdot 10H_2O$ and 100 cc. of water. The hydrous metal oxides were precipitated from solution by the addition thereto of 120 cc. of concentrated ammonium hydroxide. The precipitate obtained was filtered, washed with one liter of water and then placed in a drying oven for about 16 hours at a temperature of 120° C. The dried precipitate was then calcined in air at a temperature of 910° C. for 16 hours. The product obtained, amounting to 6.70 grams, was shown by X-ray diffraction patterns, to be the crystalline chemical compound $USb_{2.4}Ti_{0.6}O_{9-10}$. The compound obtained in this example falls within the definition of the novel compounds defined herein.

EXAMPLE IV

The procedure of Example II was repeated, except that 4.56 grams of $SbCl_3$ and 2.7 grams of $Ti_2(C_2O_4)_3 \cdot 10H_2O$ was used. The single crystalline compound $USb_{2.0}Ti_{1.0}O_{9-10}$ was obtained. The compound obtained herein also falls within the definition of the novel compounds defined herein.

EXAMPLE V

This time the procedure of Example II was repeated using 6.84 grams of $SbCl_3$, 10.04 grams of $UO_2(NO_3)_2 6H_2O$ and 8.10 grams of $Ti_2(C_2O_4)_3 \cdot 10H_2O$. A compound of the type $USb_{3-x}Ti_xO_{9-10}$, wherein x is a number between 1.0 and 1.2 was obtained, along with a small amount of $TiO_2$. Again, the predominant compound obtained herein falls within the definition of the novel compounds defined herein.

EXAMPLE VI

In this example, the run of Example IV was repeated, except that 4.56 grams of $SbCl_3$ and 10.86 grams of $Ti_2(C_2O_4)_3 \cdot 10H_2O$ were used. The product obtained did not consist substantially of a single phase, but contained the same compounds as in Example V, except that the amount of $TiO_2$ was greater.

EXAMPLE VII

The procedure of Example V was followed, except that 13.5 grams of $Ti_2(C_2O_4)_3 \cdot 10H_2O$ and 2.28 grams of $SbCl_3$ were used. In addition to the compounds found in Example V, the product also contained significant amounts of $UTiO_5$.

EXAMPLE VIII

The procedure of Example V was repeated except that no antimony compound was present and 10.04 grams of $UO_2(NO_3)_2 \cdot 6H_2O$ and 16.20 grams of $Ti_2(C_2O_4)_3 \cdot 10H_2O$ were used. The product obtained was a mixture consisting of substantial amounts of $UTiO_5$ and $TiO_2$.

EXAMPLE IX

To a solution containing 9.12 grams of $SbCl_3$, and 5.02 grams of $UO_2(NO_3)_2 \cdot 6H_2O$ and 100 cc. of water there was 40 cc. of concentrated HCl and then a solution containing 2.43 grams of $Ti_2(C_2O_4)_3 \cdot 10H_2O$ and 100 cc. of water. The hydrous metallic oxides were precipitated by the addition to the resulting solution of 120 cc. of concentrated ammonium hydroxide. The precipitate was filtered, washed with one liter of water, dried in an oven for about 16 hours at a temperature of 120° C. and then calcined in air at a temperature of 910° C. for 16 hours. The product by X-ray diffraction was found not to be a single phase but contained substantial amounts of $Sb_2O_5$ and $USb_3O_{10}$ and a lesser amount of $TiO_2$.

EXAMPLE X

Antimony powder (12.18 grams) was added to 61 grams of concentrated nitric acid at 95° C. over a period of 15 minutes, the mixture was boiled for five minutes, diluted with 50 grams of distilled water and filtered. The filter cake was washed once with 10 grams of distilled water then added to 7.01 grams of $U_3O_8$, 5.10 grams of nitric acid and 14.4 grams of distilled water. The mixture was stirred at room temperature and an aqueous ammonia solution having a specific gravity of 0.880 was added dropwise thereto until the pH reached 6.5. The resulting suspension was filtered and the precipitate was washed twice by resuspension for 15 minutes in 50 grams of distilled water containing 0.025 gram of carboxymethyl cellulose. The washed filter cake was suspended in 1000 grams of distilled water and a solution containing 3.41 grams of tetranormalpropyl orthotitanate $[(CH_3CH_2CH_2)_4TiO_4]$ in 87.9 grams of benzene was added dropwise. The suspension was stirred for one hour, filtered and the precipitate washed once by resuspension in 100 grams of water. The filter cake was dried at 110° C. for 15 hours and sieved to pass 30 mesh, mixed with 0.37 gram of graphite and then pelleted. The pellets were heated in air from 300° to 800° C. at the rate of 21° C. per hour and held at a temperature of 800° C. for 16 hours. The product by X-ray diffraction was found not to be a single phase but contained the following crystalline compounds: $Sb_2O_5$, $USb_3O_{10}$, $USbO_5$ and smaller amounts of $TiO_2$ and $SB_2O_4$.

EXAMPLE XI

To one liter of water there was added 91.24 grams of $SbCl_3$ and then 400 cc. of concentrated HCl. To this solution there was added a solution containing 100 cc. of water and 100.46 grams of $UO_2(NO_3)_2 \cdot 6H_2O$ and then a solution containing one liter of water and 64.44 grams of $ZrOCl_2 \cdot 8H_2O$. To obtain the corresponding metal oxide precipitates, there was added to the resulting solution 1200 cc. of concentrated ammonium hydroxide. The precipitate obtained was washed with 10 liters of water and then placed in a drying oven for about 16 hours at a temperature of 120° C. The dried precipitate was then calcined in air at a temperature of 910° C. for 16 hours. The product obtained was found by X-ray diffraction to be the crystalline chemical compound $USb_2ZrO_{9.10}$. The compound obtained in this example falls within the definition of the novel compounds defined herein.

EXAMPLE XII

To a solution containing one liter of water and 104.9 grams of $SbCl_3$ there was added 400 cc. of concentrated HCl, a solution containing one liter of water and 50.21 grams of $UO_2(NO_3)_2 \cdot 6H_2O$ and then a solution containing 400 cc. of water and 32.23 grams of $ZrOCl_2 \cdot 8H_2O$. The metal oxides were precipitated by the addition to the resulting solution of 1200 cc. of concentrated ammonium hydroxide. The precipitate was filtered, washed with four liters of water, dried in an oven for about 16 hours at a temperature of 120° C. and then calcined in air at a temperature of 910° C. for 16 hours. The product by X-ray diffraction was found not to be a single phase but contained substantial amounts of $Sb_2O_5$ and $USb_{3-x}Zr_xO_{10}$, wherein x is a number between 0.25 and 1.0.

Each of the above catalysts was used to prepare acrylonitrile as follows. A 0.5 ml. sample of 20–40 mesh catalyst was weighed and charged to a 0.64 cm. O.D. X 0.48 cm. I.D. tubular stainless-steel microreactor. The reactor was placed in an electric furnace. Air was flowed over the catalyst at the rate of 32.5 cc-STP $min^{-1}$ as the furnace was heated to about 450° C. When the furnace temperature reached 450° C., the reaction was carried out in cyclic fashion. The ammonia and propylene flows were started at 3.0 and 2.5 cc-STP $min^{-1}$, respectively. The furnace temperature was adjusted so that the reaction temperature, as measured by a sheathed thermocouple located within the catalyst bed, was 475° C. After 15 minutes on-stream, the product stream was sampled and then analyzed by gas chromatography. After another 15 minutes on-stream, the propylene and ammonia flows were shut off. The catalyst was regenerated by allowing the air flow to continue for 30 minutes. Propylene and ammonia flows were then resumed to begin the next on-stream period. This procedure was repeated for five or six cycles.

Thus propylene, air and ammonia were reacted at atmospheric pressure in a 1.0:13:1.2 molar ratio at a contact time of 0.28 to 0.29 second.

Average values are reported in Table I for percent conversion, percent selectivity, percent yield, and relative activity. These are defined as:

$$\text{Percent Conversion} = \frac{\text{moles of propylene converted}}{\text{moles of propylene fed}} \times 100$$

$$\text{Percent Selectivity} = \frac{\text{moles of acrylonitrile produced}}{\text{moles of propylene reacted}} \times 100$$

$$\text{Percent Yield} = \frac{\text{moles of acrylonitrile produced}}{\text{moles of propylene fed}} \times 100$$

$$\text{Relative Activity} = \frac{Ln(1 - X)^{-1}}{(0.3594) \text{ (wt. of catalyst)}}$$

where x is the mole fraction of propylene converted.

TABLE I

| Run No. | Catalyst From Example | Stoichiometry U | Sb | Ti | Zr | Grams of Catalyst | Mol Per Cent Propylene Converted | Per Cent Selectivity To Acrylonitrile | Acrylonitrile Yield | Relative Activity |
|---|---|---|---|---|---|---|---|---|---|---|
| 1  | I    | 1.0 | 4.6 | 0   | 0   | 0.431 | 16.0 | 82.1 | 13.1 | 1.1  |
| 2  | II   | 1.0 | 3.0 | 0   | 0   | 0.495 | 16.3 | 80.3 | 13.1 | 1.0  |
| 3  | III  | 1.0 | 2.4 | 0.6 | 0   | 0.638 | 61.3 | 90.6 | 55.5 | 4.1  |
| 4  | IV   | 1.0 | 2.0 | 1.0 | 0   | 0.838 | 88.7 | 89.0 | 78.9 | 7.2  |
| 5  | V    | 1.0 | 1.5 | 1.5 | 0   | 0.466 | 92.8 | 77.4 | 71.8 | 15.7 |
| 6  | VI   | 1.0 | 1.0 | 2.0 | 0   | 0.710 | 50.8 | 46.3 | 23.5 | 2.8  |
| 7  | VII  | 1.0 | 0.5 | 2.5 | 0   | 0.678 | 25.3 | 26.7 | 6.8  | 1.2  |
| 8  | VIII | 1.0 | 0   | 3.0 | 0   | 0.570 | 17.5 | 27.2 | 4.8  | 0.9  |
| 9  | IX   | 1.0 | 4.0 | 0.9 | 0   | 0.563 | 33.7 | 58.4 | 19.7 | 2.0  |
| 10 | X    | 1.0 | 4.0 | 0.9 | 0   | 0.656 | 45.7 | 84.5 | 38.6 | 2.6  |
| 11 | XI   | 1.0 | 2.0 | 0   | 1.0 | 0.652 | 92.8 | 79.4 | 73.7 | 11.2 |
| 12 | XII  | 1.0 | 4.6 | 0   | 1.0 | 0.585 | 32.2 | 82.6 | 26.6 | 1.5  |

The data in Table I amply emphasize the uniqueness of the novel composition defined herein in the preparation of acrylonitrile. Note that when the novel composition of Examples III, IV, V and XI were used in Runs Nos. 3, 4, 5 and 11, respectively, to convert propylene, air and ammonia to acrylonitrile exceedingly high yields were obtained within the exceedingly short period of 0.3 second. The remaining catalysts, which did not fall within the scope of the novel catalysts herein, resulted in exceedingly poor yields of acrylonitrile when used in the same process.

An additional series of runs was carried out, this time using the catalyst prepared in Example IV to show the effect of temperature of the novel catalysts herein in the ammoxidation reaction defined above. In all of the runs summarized below in Table II except Run No. 18, the molar ratio of propylene to air to ammonia was 1.0:11.0:1.1; in the latter run the corresponding ratio was 1.0:10.0:1.0

TABLE II

| Run No. | 13 | 14 | 15 | 16 | 17 | 18 | 19 | 20 |
|---|---|---|---|---|---|---|---|---|
| Temperature, ° C. | 401 | 426 | 455 | 475 | 475 | 475 | 486 | 495 |
| Contact Time, Seconds | 0.73 | 0.71 | 0.68 | 0.41 | 0.65 | 0.72 | 0.40 | 0.40 |
| Mol Per Cent Propylene Converted | 34.9 | 70.4 | 87.7 | 93.1 | 97.6 | 98.9 | 97.0 | 97.9 |
| Selectivity To Acrylonitrile | 78.6 | 83.8 | 86.9 | 87.7 | 86.5 | 84.1 | 87.8 | 83.0 |
| Acrylonitrile Yield | 27.5 | 59.0 | 76.4 | 81.7 | 84.4 | 83.2 | 85.2 | 81.2 |

The data in the above table show that the novel catalyst is effective over a wide temperature range in the preparation of acrylonitrile. Although yields were somewhat low in Run No. 13 this is due to the relatively low conversions of propylene. An increase in contact time would result in higher propylene conversion and accordingly increased acrylonitrile yield. In general, however, while a relatively low temperature, as low as 401° C., or even less, can be used, it can be seen that best results are obtained when the novel catalysts herein are used in the ammoxidation reaction in a temperature range of about 450° to about 495° C.

An additional series of runs was made, using catalysts containing varying amounts of uranium, antimony and zirconium, in the preparation of acrylonitrile from propylene, air and ammonia. The catalysts were prepared by first dissolving $UO_2(NO_3)_2 \cdot 6H_2O$, $SbCl_3$ and $ZrO(C_2H_3O_2)_2$ in hydrochloric acid. To this solution there was then added ammonium hydroxide until the pH thereof reached 8.0, at which point precipitates of the hydrous metallic oxides were obtained. The precipitate was recovered by filtration, washed twice with water, dried overnight at 120° C. and then calcined at 910° C. for 16 hours. The product obtained in each was used to convert propylene, air and ammonia to acrylonitrile following the procedure of Runs Nos. 1 to 12. The data obtained are summarized below in Table III.

TABLE III

| Run No. | Stoichiometry Based on Starting Materials U | Sb | Zr | Grams Of Catalyst | Mol Per Cent Propylene Converted | Per Cent Selectivity To Acrylonitrile | Acrylonitrile Yield | Relative Activity |
|---|---|---|---|---|---|---|---|---|
| 21 | 1.0 | 2.0 | 1.50 | 0.922 | 49.6 | 82.9 | 41.1 | 2.1 |
| 22 | 1.0 | 2.5 | 0.75 | 0.418 | 61.0 | 87.8 | 53.6 | 6.3 |
| 23 | 1.0 | 3.0 | 2.24 | 0.954 | 42.9 | 86.4 | 37.1 | 1.6 |
| 24 | 1.0 | 0   | 4.50 | 1.085 | 19.6 | 7.8  | 15.3 | 0.6 |
| 25 | 1.0 | 5.0 | 0.75 | 0.532 | 19.5 | 89.1 | 17.4 | 1.1 |
| 26 | 1.0 | 2.0 | 1.00 | 0.496 | 82.0 | 83.5 | 68.4 | 9.6 |
| 27 | 1.0 | 2.5 | 0.5  | 0.472 | 69.7 | 88.6 | 61.8 | 7.0 |
| 28 | 1.0 | 1.5 | 1.5  | 1.087 | 70.6 | 63.4 | 44.8 | 3.1 |

The above data further show in Runs Nos. 22, 26, 27 and 28 that when the novel catalyst herein is used to convert propylene to acrylonitrile, the novel catalyst possesses an excellent activity and excellent acrylonitrile yields are obtained.

The novel catalyst of this invention can be combined with a binder or support, such as silica, in any conventional manner to make the catalyst attrition resistant so that it can be used in a fluidized bed reactor. The preparation and use of such catalyst is exemplified by the following run.

RUN NO. 29

One liter of concentrated hydrochloric acid was added to a solution containing 114.05 grams of $SbCl_3$ and 125.53 grams of $UO_2(NO_3) \cdot 6H_2O$. To this solution there was added a solution containing 100.54 grams of titanium sulfate and 2500 cc. of water. When three liters of concentrated ammonium hydroxide was added to the resulting solution a yellow precipitate was formed. The precipitate was recovered by filtration and then washed with 25 liters of water. The filter cake, amounting to 24.8 weight percent solids, was combined with 549.33 grams of LUDOX AS (an ammonia-stabilized silica sol made and sold by duPont, Wilmington, Del.). To make a 10 weight percent solids solution 1942 grams of water was added to the mixture of filter cake and LUDOX AS. The resultant mixture was sieved through a 30-mesh screen and spray dried. The bottoms and overhead were then mixed and oven dried overnight and then calcined at 910° C. for 16 hours to obtain a product containing 50 weight percent $USb_2TiO_{10}$ and 50 weight percent $SiO_2$. A small portion of this catalyst, amounting to about two grams, was pressed into a pellet and subsequently crushed and sieved to obtain 20 to 40 mesh particles for testing in a one cc. fixed bed microreactor. One milliliter of this catalyst, amounting to 0.696 gram, was placed in the reactor and propylene was converted to acrylonitrile as in Runs Nos. 1 to 12 over a period of 0.57 second, with a propylene conversion of 80.7 percent, acrylonitrile selectivity of 87.2 percent and acrylonitrile yield of 70.4 percent.

Although the novel catalyst herein has been shown to be very effective in the ammoxidation of propylene to acrylonitrile, the catalyst can also be used advantageously in other ammoxidation reactions such as the ammoxidation of isobutylene to methacrylonitrile, and in oxidation reactions, such as oxidation reactions converting propylene to acrolein, isobutylene to methacrolein, butene-1 or butene-2 to 1,3-butadiene, and isoamylenes to isoprene.

Obviously, many modifications and variations of the invention, as hereinabove set forth, can be made without departing from the spirit and scope thereof, and, therefore, only such limitations should be imposed as are indicated in the appended claims.

We claim:

1. A process for preparing acrylonitrile which comprises reacting at an elevated temperature in the vapor phase propylene, oxygen and ammonia over a catalyst consisting essentially of a compound defined by the formula:

$$USb_{3-x}A_xO_{9-10},$$

wherein A is a Group IV B element, x is the number about 0.25 to about 1.50, said catalyst having been prepared by heating a mixture containing (1) oxides or uranium, antimony and an element from Group IV B of the Periodic Table or (2) compounds of said elements that will decompose or be converted to said oxides during said heating, wherein the atomic ratio of antimony to uranium is about 1.35:1 to about 2.75:1, the atomic ratio of the Group IV B element to uranium is about 0.25:1 to about 1.65:1 and the atomic ratio of the sum of antimony and Group IV B element to uranium is about 3.5:1 to about 2.5:1, at a temperature of at least about 850° C. for about 15 minutes to about 24 hours.

2. The process of claim 1 wherein the Group IV B element in said compound is titanium.

3. The process of claim 1 wherein the Group IV B element in said compound is zirconium.

4. The process of claim 1 wherein the Group IV B element in said compound is hafnium.

5. The process of claim 1 wherein said elevated temperature is in the range of about 375° to about 525° C.

6. The process of claim 1 wherein said elevated temperature is in the range of about 450° to about 495° C.

7. The process of claim 1 wherein said reactants are maintained within said temperature range at a contact time of at least about 0.01 second.

8. The process of claim 1 wherein said reactants are maintained within said temperature range at a contact time of about 0.1 to about 15 seconds.

9. The process of claim 1 wherein the molar ratio of oxygen to propylene is about 0.5:1 to about 5:1.

10. The process of claim 1 wherein the molar ratio of oxygen to propylene is about 1:1 to about 2:1.

11. The process of claim 1 wherein the molar ratio of ammonia to propylene is greater than about 0.9:1 but no greater than about 1.5:1.

12. The process of claim 1 wherein said compound is combined with silica.

13. The process of claim 1 wherein in the mixture being heated the atomic ratio of antimony to uranium is about 1.5:1 to about 2.5:1, the atomic ratio of the Group IV B element to uranium is about 0.5:1 to about 1.5:1 and the atomic ratio of the sum of the antimony and Group IV B element to uranium is about 3.3:1 to about 2.8:1.

* * * * *